(12) United States Patent
Vermeulen

(10) Patent No.: US 9,723,993 B2
(45) Date of Patent: Aug. 8, 2017

(54) FREQUENCY DOMAIN TIME RESOLVED FLUORESCENCE METHOD AND SYSTEM FOR PLAQUE DETECTION

(71) Applicant: KONINKLIJKE PHILIPS N.V., Eindhoven (NL)

(72) Inventor: Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 144 days.

(21) Appl. No.: 14/442,285

(22) PCT Filed: Dec. 9, 2013

(86) PCT No.: PCT/IB2013/060739
§ 371 (c)(1),
(2) Date: May 12, 2015

(87) PCT Pub. No.: WO2014/097045
PCT Pub. Date: Jun. 26, 2014

(65) Prior Publication Data
US 2016/0270666 A1 Sep. 22, 2016

Related U.S. Application Data

(60) Provisional application No. 61/739,500, filed on Dec. 19, 2012.

(51) Int. Cl.
*A61B 5/00* (2006.01)
*A61B 1/04* (2006.01)
(Continued)

(52) U.S. Cl.
CPC ............ *A61B 5/0088* (2013.01); *A61B 1/043* (2013.01); *A61B 1/045* (2013.01); *A61B 1/063* (2013.01);
(Continued)

(58) Field of Classification Search
CPC .......... A61B 5/0088; A61B 2562/0238; A61B 5/0071; A61B 6/145; A61B 5/4547;
(Continued)

(56) References Cited

U.S. PATENT DOCUMENTS 5,382,163 A   1/1995  Putnam
6,024,562 A   2/2000  Hibst et al.
(Continued)

OTHER PUBLICATIONS

Walsh et al: "Ultraviolet-Induced Fluorescence:Shedding New Light on Dental Biofilms and Dental Caries": Australasian Dental Practice, Nov./Dec. 2007, vol. 18, No. 6, p. 56-60.
(Continued)

*Primary Examiner* — Deborah Malamud

(57) ABSTRACT

A dental implement is presented including a body portion, at least one oscillator (210), and at least one light source (220) driven by the at least one oscillator and configured to emit at least one excitation light having a plurality of components modulated at a plurality of frequencies. The dental implement further includes at least one optical unit for removing reflected excitation light and receiving a fluorescence light beam from the teeth, and a detector (270) configured to receive the fluorescence light beam for detecting plaque and communicating plaque identification information of the teeth based on frequency domain lifetime measurements.

15 Claims, 5 Drawing Sheets

(51) Int. Cl.
*A61B 1/045* (2006.01)
*A61B 1/06* (2006.01)
*A61B 1/24* (2006.01)

(52) U.S. Cl.
CPC .......... *A61B 1/0646* (2013.01); *A61B 1/0684* (2013.01); *A61B 1/24* (2013.01); *A61B 5/0071* (2013.01); *A61B 5/4547* (2013.01)

(58) Field of Classification Search
CPC . A61B 5/4836; A61B 5/7228; A46B 15/0036; A46B 15/0044; A61C 1/0015
See application file for complete search history.

(56) References Cited

U.S. PATENT DOCUMENTS

| | | | |
|---|---|---|---|
| 8,027,709 B2 * | 9/2011 | Arnone | A61B 5/0088 |
| | | | 433/29 |
| 8,702,422 B2 * | 4/2014 | Binner | A46B 15/0002 |
| | | | 433/216 |
| 2011/0314618 A1 | 12/2011 | Binner et al. | |

OTHER PUBLICATIONS

Gerritsen et al:"Fluorescence Lifetime Imaging of Oxygen in Denetal Biofilm"; Proceedings of SPIE, Vo. 4164, Jan. 2000, pp. 70-78.
De Oliveira et al: "Time-Resolved Fluoresence Spectroscopy of White-Spot Caries in Human Enamal"; Applied Optics, Optical Society of America, vol. 49, No. 12, pp. 2244-2249.
Koenig et al: "Laser-Induced Autofluorescence for Medical Diagnosis"; Journal of Fluorescence, vol. 4, No. 1, 1994, pp. 17-40.

* cited by examiner

FREQUENCY DOMAIN TIME RESOLVED FLUORESCENCE METHOD AND SYSTEM FOR PLAQUE DETECTION

CROSS-REFERENCE TO PRIOR APPLICATIONS

This application is the U.S. National Phase application under 35 U.S.C. §371 of International Application No. PCT/IB2013/060739, filed on Dec. 9, 2013, which claims the benefit of U.S. Provisional Patent Application No. 61/739,500, filed on Dec. 19, 2012. These applications are hereby incorporated by reference herein.

TECHNICAL FIELD

The present disclosure relates to dental implements, such as toothbrushes or airfloss. More particularly, the present disclosure relates to an electronic toothbrush for detecting plaque based on frequency domain lifetime measurements.

BACKGROUND ART

Toothbrushes are designed to clean teeth by removing bio-films and food debris from teeth surfaces and interproximal regions in order to improve oral health. A wide variety of electronic toothbrush designs have been created to provide improved brushing performance by increasing the speed of the brush head and using sonic vibration, and in some cases ultrasonic vibration.

Modern toothbrushes are very efficient at removing plaque. The consumer need only brush in the problem area for a few seconds to lift off plaque that is being brushed. However, without feedback the consumer may move on to another tooth before plaque has been completely removed. Thus, an indication of plaque levels on the teeth is highly desirable.

Despite improvements in toothbrush designs, it is still difficult to reach interproximal regions. Plaque disclosing dyes are available to help consumers identify areas where plaque builds up and where brushing needs to be concentrated. However, these dyes have not been well-received by consumers.

Therefore, there is an increasing need to develop dental implements that may identify plaque and communicate these problem areas, in real-time and continuously, to the user, so that the user may concentrate his/her brushing efforts in these problem areas.

SUMMARY

The invention is defined by the independent claims; the dependent claims define advantageous embodiments.

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In accordance with aspects of the present disclosure, a dental implement is presented. The dental implement includes a body portion; at least one oscillator; at least one light source driven by the at least one oscillator and configured to emit at least one excitation light having components modulated at a plurality of frequencies; at least one optical unit for removing reflected excitation light and receiving a fluorescence light beam from the teeth; and a detector configured to receive the fluorescence light beam for detecting plaque and communicating plaque identification information of the teeth based on frequency domain lifetime measurements.

According to an aspect of the present disclosure, the at least one light source is a light emitting diode having wavelengths ranging between about 400 nm and 500 nm. Alternatively, the at least one light source is a diode laser.

According to a further aspect of the present disclosure, the dental implement further comprises an optical excitation cleanup filter. The optical excitation cleanup filter may be a narrow bandpass filter.

According to another aspect of the present disclosure, the detector includes at least a photodetector and an amplifier.

According to yet another aspect of the disclosure, a first optical element configuration is positioned between the at least one light source and an optical fluorescence emission cleanup filter, and a second optical element configuration is positioned between the at least one optical unit and the teeth.

According to a further aspect of the disclosure, a controller drives the at least one oscillator. Alternatively, the at least one oscillator is incorporated within a controller. The controller includes a heterodyning stage to down convert signals to an intermediate frequency (IF) band.

According to another aspect of the disclosure, the at least one optical unit is at least one of a long pass beam splitter, a shortpass beam splitter, a bandpass filter, a band reject filter, and a dichroic beam splitter.

According to yet a further aspect of the disclosure, a method of detecting plaque on teeth via a dental implement having a body portion is presented. The method includes the steps of providing at least one oscillator; driving at least one light source by the at least one oscillator, the at least one light source configured to emit at least one excitation light having components modulated at a plurality of frequencies; removing reflected excitation light via at least one optical unit; receiving a fluorescence light beam from the teeth; and detecting, via a detector, plaque and communicating plaque identification information of the teeth based on frequency domain lifetime measurements.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

Figure 1A:
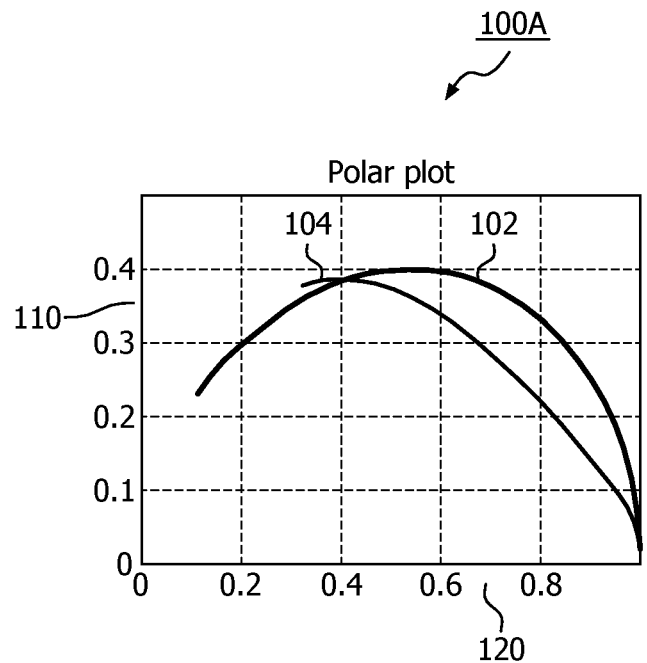
FIGS. 1A and 1B illustrate a polar plot and a plaque vector plot, respectively, according to the present disclosure.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION OF EMBODIMENTS

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The present disclosure describes various embodiments of systems, devices, and methods for helping users clean their teeth, in particular, by informing users whether they are indeed removing plaque from their teeth and if they have fully removed the plaque, providing both reassurance and coaching the users into good habits. Preferably the information is provided in real-time during brushing/cleaning, otherwise consumer acceptance is likely to be low. For example, it is useful for a dental implement to provide the user with a signal when the tooth the user is brushing is considered clean, so that the user may move on to the next tooth, which may require additional brushing due to plaque build-up. This may reduce the user's brushing time, but also leads to a better and more efficient brushing routine that focus the user's attention to specific problem areas of the teeth (e.g., that have plaque).

In accordance with the present disclosure, a user is able to detect plaque with an electronic toothbrush, i.e., in a vibrating brushing system surrounded with toothpaste foam. The plaque detection system is configured to provide a clear contrast between a surface with the removable plaque layers and a cleaner pellicle/calculus/dental filling/tooth surface.

In accordance with the present disclosure, there is provided a way to detect plaque in real-time during the brushing routine. The exemplary embodiments of the present disclosure implement plaque detection based on time resolved fluorescence, in particular frequency domain lifetime measurements.

In accordance with the present disclosure, a method is provided to determine the amount of plaque on an arbitrary set of teeth, whether with or without dental fillings. It is further an object of the present disclosure to enable the plaque detection during brushing, whether with or without the presence of toothpaste. It is also the object of the present disclosure to make the plaque detection method independent of small distance variations between the brush-head and the teeth. One skilled in the art may contemplate a plurality of different configurations for using such plaque detection system based on frequency domain lifetime measurements.

In accordance with the present disclosure, the elements of the plaque detection system include at least an oscillator, an excitation light source driven by the oscillator, and an optical excitation cleanup filter followed by a photodetector connected to a processing unit. The issue of varying dentine time constants is handled by a one-time calibration performed on a clean tooth. This is possible because the enamel/dentine lifetime variation within one person's set of teeth is much less than the variation measured for a large population of people. A measurement relative to clean dentine of a tooth also automatically minimizes errors caused by variations in transfer functions of the plaque detection system itself caused by, for example, temperature or power supply variations or, for example, by component variations inherent to mass production.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments will be described below while referencing the accompanying figures. The accompanying figures are merely examples and are not intended to limit the scope of the present disclosure.

Figure 1B:
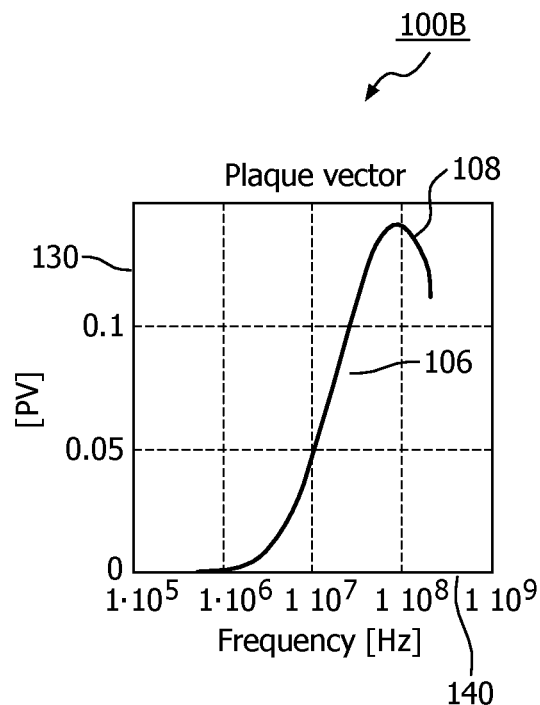

FIGS. 1A and 1B illustrate a polar plot and a plaque vector plot, respectively, according to the present disclosure.

Referring to FIGS. 1A and 1B, a first method of the present disclosure for detecting plaque build-up utilizes a plot of $M \cdot \sin(\Phi)$ (y-axis) versus $M \cdot \cos(\Phi)$ (x-axis), where, M, is the de-modulation ratio and, $\Phi$, is the phase delay of the fluorescence emission with respect to the excitation. Demodulation is defined as the ratio of the modulation index of the emission intensity versus the modulation index of the excitation intensity (with modulation index $mi = AC/DC$). The excitation light source is frequency modulated within a range between about 200 kHz to 200 MHz and the detected fluorescence is plotted as $M \cdot \sin(\Phi)$ versus $M \cdot \cos(\Phi)$ (e.g., the 90° phase shifted component vs. in-phase part of the response). However, one skilled in the art may contemplate a plurality of different frequency ranges for modulation/demodulation. Such a plot is referred to as a polar plot, as shown in FIG. 1A. In the polar plot 100A, clean dentine is described as a locus starting near [1:0] at low frequencies and progressing towards the origin for higher frequencies, as illustrated by line 102. Also, the phase angle is the angle between the x-axis and the location at a given frequency and the distance from the origin provides for the magnitude of the response.

Referring to FIG. 1A, locus 104 describes the results of dentine covered with a plaque layer that also starts near [1:0], yet depicts a different path at increasing frequencies, as shown by line 104. The distance between these two loci for each modulation frequency (referred to as the plaque-vector PV, shown as line 106 in FIG. 1B) is a measure for the amount of plaque present on the teeth of a user. At a certain frequency range the PV reaches a maximum 108, as shown in FIG. 1B. This reveals the frequency modulation or FM range for detecting the plaque on the teeth. In this case, the optimum frequency sweep range is about 40 to 200 MHz. However, one skilled in the art may contemplate a plurality of different frequency ranges based on the application at hand. It is noted that in FIG. 1B, the x-axis 140 represents modulation frequency, whereas the y-axis 130 represents the length of the plaque vector which is a measure of plaque levels.

Moreover, various dental filling materials may alter the shape of measured polar plot 100A. Since each dental filling material has its own known decay time, the influence of filling materials on the plaque detection may be minimized according to this exemplary embodiment. The optimum sweep range may be limited between about 40 to 100 MHz to detect plaque reliably. However, one skilled in the art may contemplate any suitable frequency sweep range. Moreover, when the detection system is calibrated on a clean dentine site, the loci in the polar plots of subsequently measured plaque-free dentine/enamel sites do not leave the low frequency starting point because phase and demodulation is calibrated to 0 and 1 for each frequency. Sites in the mouth of a user covered with plaque show a locus departing from the low frequency starting point, thus enabling quick and efficient plaque detection. Since the variation in enamel/dentine decay times within one person's set-of-teeth is limited, this method enables a large variation of plaque to be determined.

Therefore, the first method described above relates to a sweep of many frequencies. The method described in this paragraph, is a second method, that uses a limited number of frequencies, whereas the method described in following paragraph, as a third method, describes the use of a minimum number of two modulation frequencies. In the second method, calibration on a clean enamel/dentine site may be used to reduce the enamel/dentine lifetime variation. Plaque may be detected measuring M and Φ at a limited number of discrete frequencies in the range of about 20 to 200 MHz. The teeth are excited with these frequencies sequentially or simultaneously. The presence of plaque is determined by the length and direction of the plaque vectors per frequency. The length is an indication of the intensity (amount/density), while the angle is a measure for the species and may be used to distinguish plaque from fillings or other dental implants.

According to a third method of the present disclosure for determining plaque build-up, an excitation light source modulated with at least two frequencies sequentially or simultaneously is used. The lower frequency is chosen such that the demodulation caused by the enamel/dentine and plaque is negligible. Since the time constant of enamel/dentin is dominant, the preferred low frequency component is below 1 MHz. Such a frequency gives less than 1% demodulation for decay times up to 10 ns so that the measured AC component is related to a demodulation of M=1. The second (or subsequent) frequency is chosen in the range between about 20 to 200 MHz. Now only the AC part is required to be measured since the demodulation may be calculated from the AC ratios (e.g., DC attenuation is frequency independent and $m_{LF}=1$).

Figure 2:
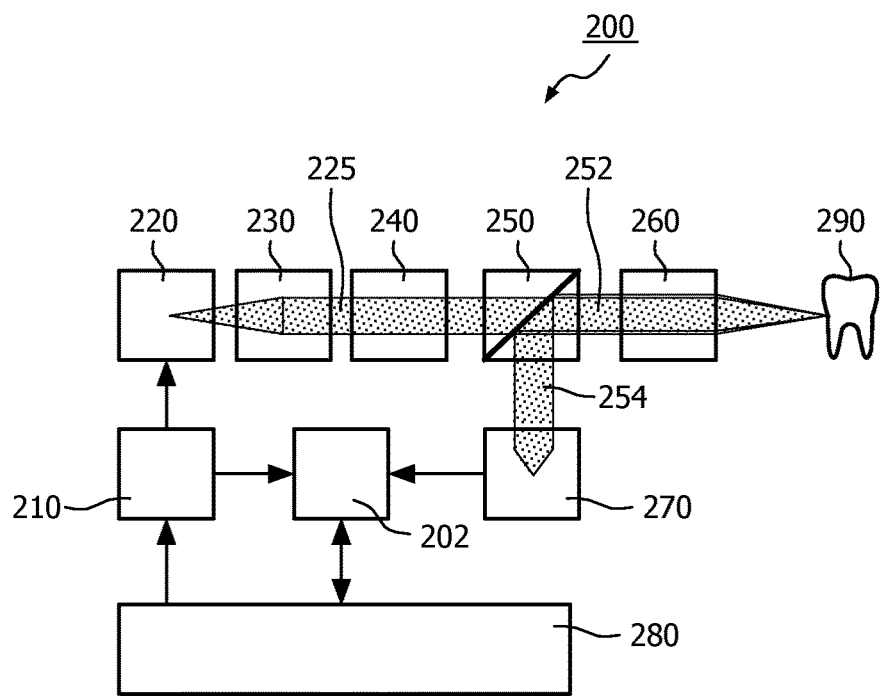
FIG. 2 is a schematic diagram illustrating a plaque detection technique based on a fluorescence lifetime measurement, where a single detector is shown, according to the present disclosure.

FIG. 2 depicts a schematic diagram 200 illustrating a plaque detection technique based on a fluorescence lifetime measurement, where a single detector is shown, according to the present disclosure.

In FIG. 2, an oscillator 210 is depicted for driving a light source 220. The light source 220 generates an excitation light 225 passing through a first optical element configuration 230, a cleanup filter 240, and a dichroic beam splitter 250. The beam splitter 250 allows the excitation light 225 to pass straight through. The returning light 252 from the teeth 290 is split so that only the fluorescent light 254 is received by the detector 270. The excitation light 225 is directed through a second optical element configuration 260 and onto teeth 290, whereas the fluorescent light 254 is directed toward a detector 270. The detector 270 may include an amplifier 202. It is also contemplated that the oscillator 210 is driven by a controller 280.

The light source 220 generating the excitation light 225 is preferably an LED of 405 nm, 440 nm 470 nm or 480 nm, but other sources (e.g., diode laser) and different wavelengths are also possible (e.g., ranging between about 400 nm and 500 nm). One skilled in the art may contemplate a plurality of different lighting means operating at a plurality of different wavelengths. The diode laser may also be a vertical cavity surface emitting laser (VCSEL). The VCSEL is a type of semiconductor laser diode with laser beam emission perpendicular from the top surface, contrary to conventional edge-emitting semiconductor lasers, which emit from surfaces formed by cleaving the individual chip out of a wafer.

The optional cleanup filter 240 may be a narrow bandpass filter, which blocks any undesired wavelength from reaching the teeth 290 (e.g., UV light) or the detector 270. The dichroic beam-splitter 250 may have a sort-pass characteristic, such that the excitation light 225 is transmitted towards the teeth 290, while the emitted fluorescence light 254, having a longer wavelength, is reflected towards the detector 270. The detector 270 may include a photodetector (not shown) and an amplifier 202. The system 200 may also include a collection of focusing optics, such as lenses, CPC's (compound parabolic concentrators) or both (shown as elements 230, 260). In one exemplary embodiment, the optical elements 230, 260 of the system may be integrated into the head portion of the dental implement. However, one skilled in the art may contemplate rearranging or placing all or part of the elements of FIG. 2 either in the handle portion or the head portion of the dental implement or a combination thereof based on suitable designs. Thus, the components of FIG. 2 are not limited as to their placement on or about a dental implement.

Moreover, in another exemplary embodiment, instead of a single optical path and a beam splitter, two optical paths (e.g., excitation and detection) may be used with a high pass or bandpass or band-reject filter at the detector 270 to block the excitation light 225. The separate excitation and detection paths may be fiber guided or free space or a combination of both, e.g., free-space excitation via an LED in the brush-head and fiber detection. This is further described below with reference to FIG. 6.

The controller 280 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller, as recited, for example, in the claims. The controller may be provided as a single integrated circuit (IC) chip which may be mounted on a single printed circuit board (PCB). Alternatively, the various circuit components of the controller, including, for example, the processor, microcontroller, etc. are provided as one or more integrated circuit chips. That is, the various circuit components are located on one or more integrated circuit chips.

Figure 3:
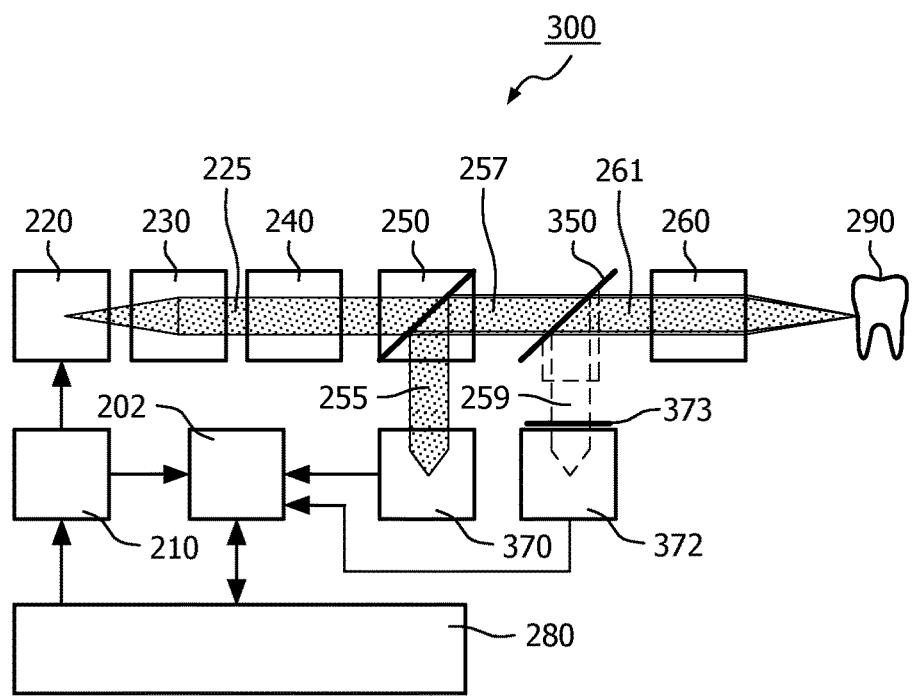
FIG. 3 is a schematic diagram illustrating a plaque detection technique based on a fluorescence lifetime measurement, where two detectors are shown, according to the present disclosure.

FIG. 3 depicts a schematic diagram 300 illustrating a plaque detection technique based on a fluorescence lifetime measurement, where two detectors are shown, according to the present disclosure.

In FIG. 3, an oscillator 210 is depicted for driving a light source 220. The light source 220 generates an excitation light 225 passing through a first optical element configuration 230, a cleanup filter 240, and two beam splitters 250, 350. The beam splitters 250, 350 allow the excitation light 225 to pass straight through. Thus, the excitation light 225 passes straight through the two beam splitters 250, 350 and excites the fluophores on the teeth and plaque. The light 261 returned from the teeth 290 and collected by the system consists of reflected excitation light (blue) 257 and fluorescence light 255 (emission with longer wavelength). On the way back into the system 300, it first reaches the low reflection beam splitter (glass) to couple out a small fraction. The remainder goes to the beam splitter 250 and towards the detector 370. The fractional part coming from the glass reflection is short (or band-) pass filtered such that only the original excitation light 259 is detected by 372. This is referred to as the reference signal.

FIG. 3 is similar to FIG. 2, however, in FIG. 3 a portion of the reflected excitation light 261 is measured separately to compensate for any drift which may cause undesired phase changes between excitation and emission signals, for example, an optical path length difference caused by distance variations or temperature effects. The extension uses a low reflection beam splitter 350 (e.g., uncoated glass) to couple out a low percentage of the received light 261. A low pass filter 373 removes the fluorescence light such that only part of the reflected excitation light 261 is received by the detector 372. This light 259 has travelled the full path length and is therefore a reference for phase.

Figure 4:
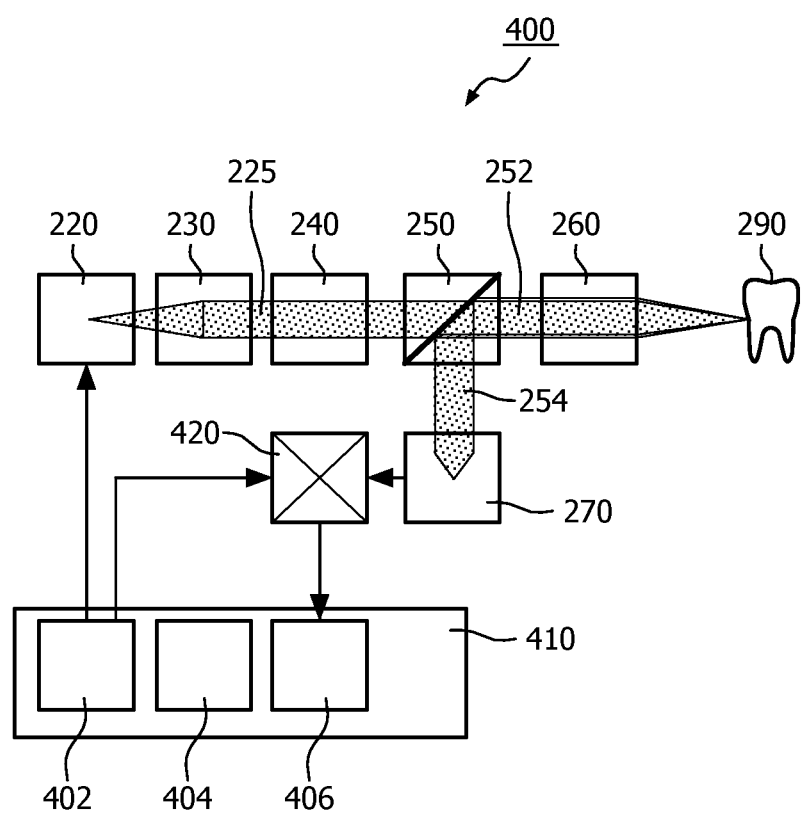
FIG. 4 is a schematic diagram illustrating a plaque detection technique based on a fluorescence lifetime measurement, where an oscillator is incorporated within the controller, according to the present disclosure.

FIG. 4 depicts a schematic diagram 400 illustrating a plaque detection technique based on a fluorescence lifetime measurement, where an oscillator is incorporated within the controller, according to the present disclosure.

In FIG. 4, an oscillator 402 is depicted for driving a light source 220. The light source 220 generates an excitation light 225 passing through a first optical element configuration 230, a cleanup filter 240, and a dichroic beam splitter 250. The beam splitter 250 allows the excitation light 225 to pass straight through. The returning light 252 from the teeth 290 is split so that only the fluorescent light 254 is received by the detector 270. The excitation light 225 is directed through a second optical element configuration 260 and onto teeth 290, whereas the fluorescent light 254 is directed toward a detector 270. The detector 270 sends a signal to a mixer 420. It is also contemplated that the oscillator 402 is incorporated within a controller 410. The controller 410 may also include a lock-in amplifier 404 and an ADC converter 406.

For all embodiments, as described with reference to FIGS. 2-4, the oscillator 410 and lock-in amplifier 404 may be implemented in the analog or digital domain. However, in accordance with FIG. 4, for the digital implementation into the controller 410, an analog heterodyning stage may be included to down convert the signals to an intermediate frequency (IF) band that is better suited for ADC conversion. Therefore, for each frequency, the digital oscillator 402 further generates a frequency with a small offset for the mixer 420, such that the low-pass filtered mixer 420 output falls within the frequency range of the ADC converter 406. In such case, all further signal processing is performing in a digital manner. Moreover, even though FIG. 4 describes the digital implementation for only one of the embodiments, it should be noted that all embodiments may be implemented this way by one skilled in the art.

Figure 5:
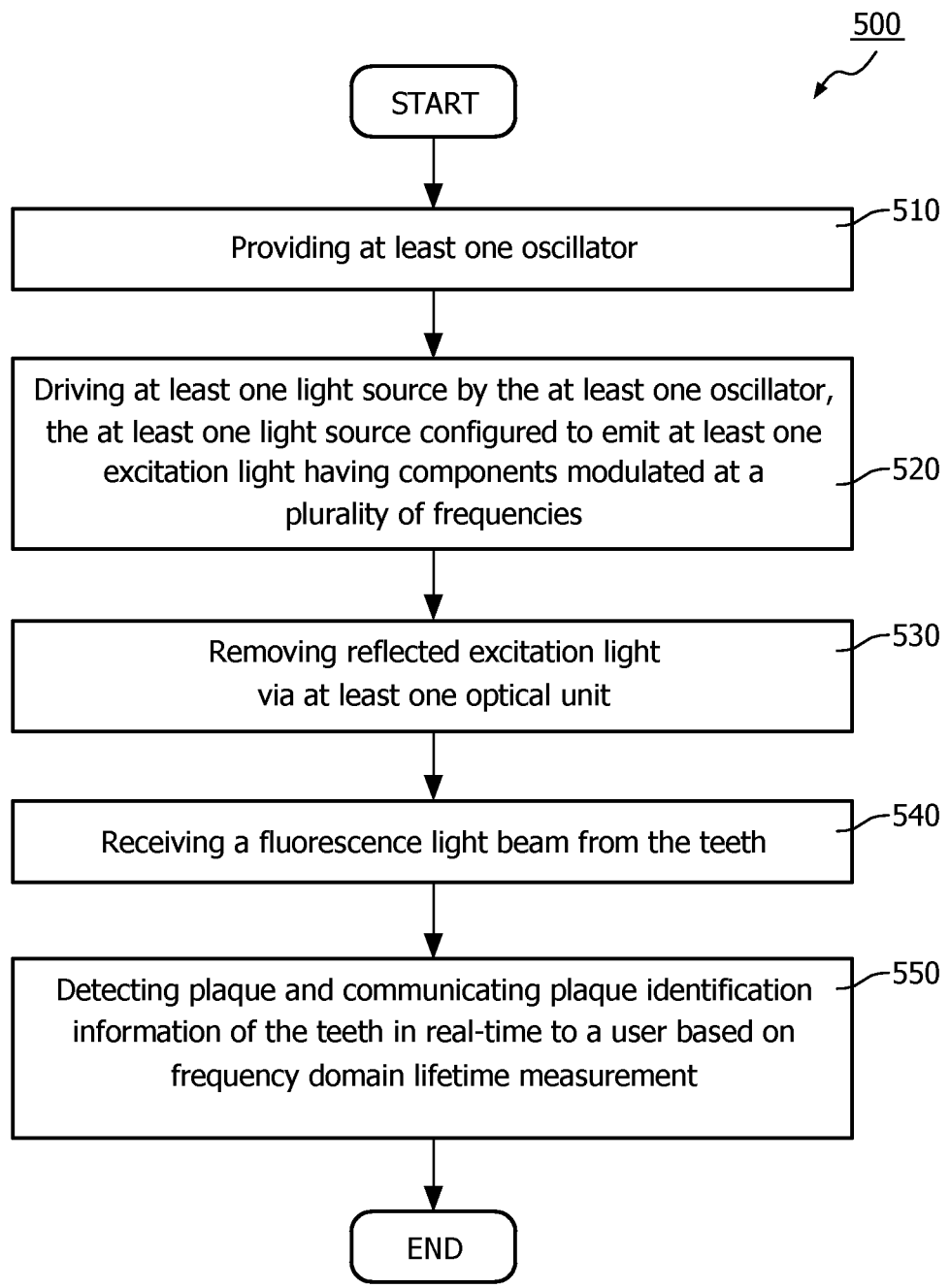
FIG. 5 is a flowchart illustrating a method of detecting plaque based on a fluorescence lifetime measurement, according to the present disclosure.

FIG. 5 is a flowchart 500 illustrating a method of detecting plaque based on a fluorescence lifetime measurement, according to the present disclosure.

The flowchart 500 includes the following steps. In step 510, an oscillator is provided. In step 520, at least one light source is driven by the at least one oscillator, the at least one light source configured to emit at least one excitation light having components modulated at a plurality of frequencies. In step 530, reflected excitation light is removed via at least one optical unit. In step 540, a fluorescence light beam is received from the teeth. In step 550, plaque is detected and plaque identification information of the teeth is communicated in real-time to a user based on frequency domain lifetime measurements. The process then ends. It is to be understood that the method steps described herein need not necessarily be performed in the order as described. Further, words such as "thereafter," "then," "next," etc. are not intended to limit the order of the steps. These words are simply used to guide the reader through the description of the method steps.

Figure 6:
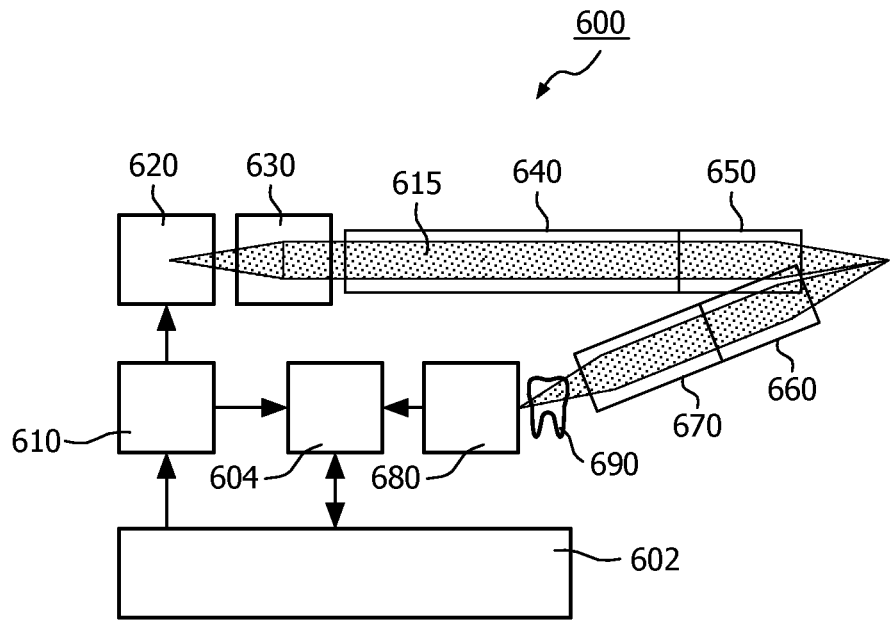
FIG. 6 is a schematic diagram of a plaque detection technique based on a fluorescence lifetime measurement, where an excitation fiber and an emission fiber are included instead of a beam splitter, according to the present disclosure.

FIG. 6 is a schematic diagram 600 of a plaque detection technique based on a fluorescence lifetime measurement, where an excitation fiber and an emission fiber are included instead of a beam splitter, according to the present disclosure.

The system 600 includes an oscillator 610 for driving a light source 620. The light source 620 generates an excitation light 615 that goes through an excitation fiber 640 and an excitation cleanup filter 650. An emission filter 660 and an emission fiber 670 are positioned between a tooth 690 and a detector 680. The detector 680 communicates with a lock-in amplifier 604. The lock-in amplifier 604 communicates with a controller 602. Additionally, an optical element configuration 630 may be positioned between the light source 620 and the excitation fiber 640. As illustrated, the emission filter 660 and the excitation cleanup filter 650 are located on the tooth side of the fibers 640, 670 to reduce or eliminate the effects of fluorescence of the fiber. However, one skilled in the art may contemplate positioning the emission filter 660 and the excitation cleanup filter 650 in various configurations. Moreover, it is also noted that the excitation cleanup filter is 650 is optional in such a configuration.

Therefore, two optical paths (e.g., excitation path and detection path) may be used with a high pass or bandpass or band-reject filter at the detector 680 to block the excitation light 615. The separate excitation and detection paths may be fiber guided or free space or a combination of both, e.g., free-space excitation via an LED in the brush-head and fiber detection.

Figure 7:
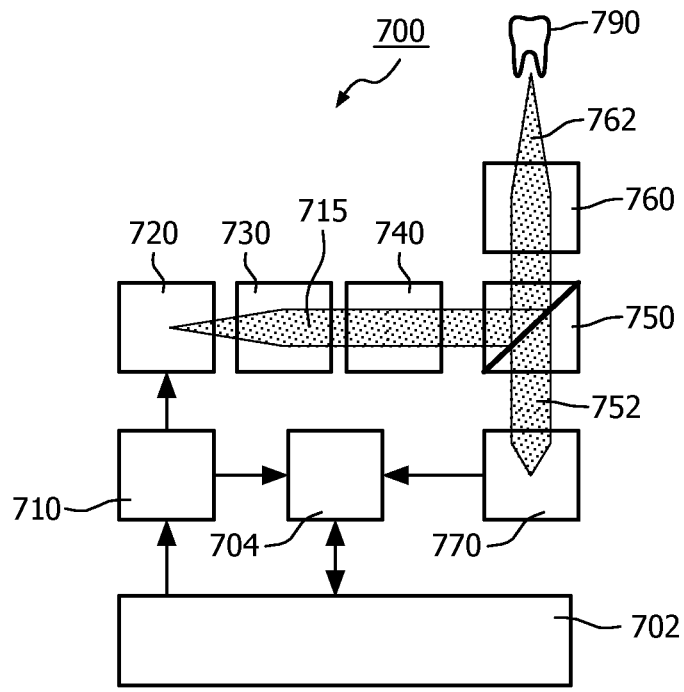
FIG. 7 is a schematic diagram of a plaque detection technique based on a fluorescence lifetime measurement, where a long pass beam splitter configuration is presented, according to the present disclosure.

FIG. 7 is a schematic diagram 700 of a plaque detection technique based on a fluorescence lifetime measurement, where a long pass beam splitter configuration is presented, according to the present disclosure.

The system 700 includes an oscillator 710 for driving a light source 720. The light source 720 generates an excitation light 715 that goes through an optical element configuration 730, a clean-up filter 740 and a beam splitter 750. The beam splitter 750 reflects the excitation light 715 towards a tooth 790. The returning light 762 is split so that only the fluorescent light 752, having a longer wavelength, is received by the detector 770. The detector 770 may communicate with a lock-in amplifier 704. It is also contemplated that the oscillator 710 is driven by a controller 702. Additionally, a second optical configuration 760 may be positioned after the beam splitter 750. The beam splitter 750 may be a long pass beam splitter, as opposed to the dichroic beam splitters shown in FIGS. 2-4.

In another embodiment, the detection system is calibrated on a clean piece of enamel/dentine for each user individually. This process maximizes the signal range because the variation in lifetime data within one set of teeth is much less than such variation within the total human population. Additionally, by calibrating out all phase delays and frequency dependent gains on the clean tooth, all following measurement results are a direct measure for the amount of plaque detected.

In summary, plaque detection is possible by measuring the fluorescence lifetime properties of teeth in the frequency domain. Dental implements using steady-state fluorescence use a DC excitation, whereas time domain lifetime devices/ use a very short pulse excitation. For the methods described in the exemplary embodiments, the excitation source is modulated, where multiple frequencies are simultaneously used or swept frequency is used. Therefore, plaque detection is based on frequency domain lifetime measurements. Moreover, it is noted that the frequency domain detection may also use the harmonic content of pulse excitation (similarly to time domain detection), but this is not practical in the frequency domain method for toothbrushes (or other CE devices or dental implements) because very sensitive and expensive detection is needed in such an embodiment using pulse excitation.

In general, the exemplary embodiments of the present disclosure specifically relate to dental implements, such as toothbrushes or airfloss. However, the exemplary embodiments of the present disclosure may be broadened by one skilled in the art to include professional dental examination devices, whereby presence of plaque may be revealed by images, sound or vibration frequency and intensity. This is applicable in fields such as dentistry, dental hygiene, and tooth whitening.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A dental implement, comprising:
at least one oscillator;
at least one light source driven by the at least one oscillator and configured to emit at least one excitation light having components modulated at a plurality of frequencies;
at least one optical unit for removing reflected excitation light and receiving a fluorescence light beam from a user's teeth based on a fluorescence of plaque itself;
a detector configured to receive the fluorescence light beam; and
a controller responsive to an output of the detector, for detecting a measure of an amount of plaque and communicating plaque identification information of the user's teeth based on frequency domain lifetime measurements as a function of the received fluorescence light beam and the excitation light having components modulated at the plurality of frequencies.

2. The dental implement according to claim 1, wherein the at least one light source is a light emitting diode having wavelengths ranging between about 400 nm and 500 nm.

3. The dental implement according to claim 1, wherein the at least one light source is a diode laser.

4. The dental implement according to claim 1, further comprising an optical excitation cleanup filter.

5. The dental implement according to claim 1, wherein the detector includes at least a photodetector and an amplifier.

6. The dental implement according to claim 1, wherein a first optical element configuration is positioned between the at least one light source and an optical fluorescence emission filter, and a second optical element configuration is positioned between the at least one optical unit and the teeth.

7. The dental implement according to claim 1, wherein the at least one optical unit is at least one of a long pass beam splitter, a short pass beam splitter, a bandpass filter, a band reject filter, a long pass filter, and a dichroic beam splitter.

8. The dental implement according to claim 1, wherein the controller is configured to control the at least one oscillator to modulate the at least one light source with one of (i) a sweep of frequencies in a range between 200 kHz to 200 MHz, (ii) a limited number of discrete frequencies in a range of 20 to 200 MHz, and (iii) a minimum number of two modulation frequencies that include (a) a lower frequency below 1 MHz and (b) a subsequent frequency in a range between 20 to 200 MHz.

9. A method of detecting plaque on teeth via a dental implement including a body portion, the method comprising:
providing at least one oscillator;
driving at least one light source by the at least one oscillator, the at least one light source configured to emit at least one excitation light toward a user's teeth, the at least one excitation light having components modulated at a plurality of frequencies;
removing excitation light reflected from the user's teeth and passing a fluorescence light beam reflected from the user's teeth, via at least one optical unit;

receiving, at a detector, the fluorescence light beam reflected from the teeth based on a fluorescence of plaque itself; and detecting, via a controller in response to an output of the detector, a measure of an amount of plaque and communicating plaque identification information of the user's teeth based on frequency domain lifetime measurements as a function of the received fluorescence light beam and the excitation light having components modulated at the plurality of frequencies.

10. The method according to claim 9, wherein the at least one light source is a light emitting diode having wavelengths ranging between about 400 nm and 500 nm.

11. The method according to claim 9, wherein the at least one light source is a diode laser.

12. The method according to claim 9, further comprising using an optical excitation cleanup filter on the at least one excitation light emitted from the at least one light source.

13. The method according to claim 9, wherein the detector includes at least a photodetector and an amplifier.

14. The method according to claim 9, wherein a first optical element configuration is positioned between the at least one light source and an optical fluorescence emission filter, and a second optical element configuration is positioned between the at least one optical unit and the user's teeth.

15. The method according to claim 9, wherein the at least one optical unit is at least one of a long pass beam splitter, a short pass beam splitter, a bandpass filter, a band reject filter, a long pass filter, and a dichroic beam splitter.

* * * * *